(12) United States Patent
Connolly et al.

(10) Patent No.: US 7,678,553 B2
(45) Date of Patent: Mar. 16, 2010

(54) SELECTION AND USE OF LACTIC ACID BACTERIA FOR REDUCING INFLAMMATION CAUSED BY HELICOBACTER

(75) Inventors: Eamonn Connolly, Lidingo (SE); Bo Mollstam, Lerum (SE)

(73) Assignee: Biogaia AB, Lerum (SE)

( * ) Notice: Subject to any disclaimer, the term of this patent is extended or adjusted under 35 U.S.C. 154(b) by 0 days.

(21) Appl. No.: 12/315,383

(22) Filed: Dec. 3, 2008

(65) Prior Publication Data

US 2009/0110670 A1    Apr. 30, 2009

Related U.S. Application Data

(62) Division of application No. 11/394,786, filed on Mar. 31, 2006, now abandoned, which is a division of application No. 10/265,859, filed on Oct. 7, 2002, now Pat. No. 7,105,336.

(51) Int. Cl.
| | |
|---|---|
| *C12Q 1/04* | (2006.01) |
| *C12Q 1/02* | (2006.01) |
| *C12Q 1/24* | (2006.01) |
| *A61K 35/74* | (2006.01) |
| *C12N 1/20* | (2006.01) |

(52) U.S. Cl. .............. 435/34; 435/29; 435/30; 435/252.1; 435/252.9; 435/373; 436/63; 424/93.45; 426/61

(58) Field of Classification Search .......... None
See application file for complete search history.

(56) References Cited

U.S. PATENT DOCUMENTS

| | | | |
|---|---|---|---|
| 5,439,678 | A | 8/1995 | Dobrogosz et al. |
| 5,458,875 | A | 10/1995 | Casas et al. |
| 5,534,253 | A | 7/1996 | Casas et al. |
| 5,837,238 | A | 11/1998 | Casas et al. |
| 5,849,289 | A | 12/1998 | Dobrogosz et al. |
| 6,051,557 | A | 4/2000 | Drucker |
| 6,613,751 | B2 | 9/2003 | Raz et al. |
| 2003/0176389 | A1 | 9/2003 | Raz et al. |
| 2005/0180962 | A1 | 8/2005 | Raz et al. |

*Primary Examiner*—Herbert J. Lilling
(74) *Attorney, Agent, or Firm*—Lynn E. Barber

(57) ABSTRACT

Strains of *Lactobacillus* which have been selected for their capability of reducing gastrointestinal inflammation, such as that due to *Helicobacter pylori*, and products derived from these strains, including agents for treatment or prophylaxis of inflammation associated with *Helicobacter pylori* for administration to humans and include conditioned media in which the selected strains have grown and protein-containing extracts of the conditioned media.

1 Claim, 2 Drawing Sheets

SELECTION AND USE OF LACTIC ACID BACTERIA FOR REDUCING INFLAMMATION CAUSED BY HELICOBACTER

CROSS-REFERENCE TO RELATED APPLICATIONS

This is a divisional patent application of U.S. patent application Ser. No. 11/394,786 filed Mar. 31, 2006, now abandoned which is a divisional application of U.S. patent application Ser. No. 10/265,859 filed Oct. 7, 2002, now U.S. Pat. No. 7,105,336 issued Sep. 12, 2006.

BACKGROUND OF THE INVENTION

1. Field of the Invention

This invention relates to use of a method for screening nonpathogenic anti-inflammatory bacterial strains, and products and methods using such strains for treatment and prophylaxis of inflammation caused by gastrointestinal bacteria such as *Helicobacter pylori*, other species of *Helicobacter*, and other inflammation-causing gastrointestinal pathogens.

2. Description of the Related Art

*Helicobacter pylori* is a spiral-shaped bacterium that colonizes the stomach by, among other things, its ability to produce urease to neutralize the acids in the stomach. Urease converts urea, of which there is an abundant supply in the stomach, to bicarbonate and ammonia, which are strong bases. This results in a cloud of acid-neutralizing bases around the *H. pylori* cells, protecting them from the acid in the stomach. The *H. pylori* cells penetrate and traverse the gastric mucus layer and attach to epithelial cells in the lining of the stomach. At least some strains of *H. pylori* have the ability to produce toxins. Infection with *H. pylori* activates the host immune system, which sends white blood cells, killer T cells and other infection-fighting agents to the area, but the body's immune system is not effective in reversing the effects of *H. pylori* in the mucus lining of the stomach. The *H. pylori* cells remain in the lining, and the immune system escalates its response to the cells, creating an inflammation if there are not sufficient anti-inflammatory mechanisms available. During the infection with *H. pylori*, cytokine intercellular signal proteins generated by the host epithelium dendritic cells, natural killer cells, T-cells and other immune defense cells propagate the immune response to the invading pathogen. Consequently, host neutrophils are attracted to and infiltrate the stomach epithelium and persist there throughout the infection. These cells generate, among other factors, reactive oxygen products, such as superoxide radicals, which lead to oxidation in the epithelial cells and consequent epithelial cell death, ulcer formation and ultimately carcinogenesis. *H. pylori* also induces leakage of nutrients from the host over the stomach epithelium providing a nutrient source to sustain the *H. pylori* cells and exacerbate the infection and its consequences. *H. pylori* is able to evade the human immune system and survive in the stomach despite the immune response of the host and the mechanisms of this evasion are the subject of current research.

Current therapy is based on eradicating *H. pylori* through antibiotics and proton pump inhibitors rather than attempting to eliminate the effects of excessive immune response of the host to the infection, such as making sufficient anti-inflammatory mechanisms available, which is the purpose of the present invention.

Thus, infection with *H. pylori* causes an increased risk of developing gastritis, gastric and duodenal ulcers, including peptic ulcer, gastric cancer, and gastric mucosa-associated lymphoid tissue lymphoma. These problems are not caused directly by the *H. pylori* cells, but by the inflammation of the stomach lining in response to the *H. pylori*. Various treatments have been used to ameliorate the symptoms of gastric and duodenal ulcers, such as treatments that reduce acid production in the stomach, combined with antibiotics. Novel vaccines against *H. pylori* has also been tried but with limited success. It is also known that other species of *Helicobacter*, as well as other gastrointestinal pathogens, can cause gastrointestinal inflammation.

In a recent research article, researchers studying *H. pylori* infections concluded that infection by *H. pylori* elicits gastric mucosal sialylation as part of the chronic inflammatory response and that many virulent strains are thus better able to attach to the inflamed site (*Science* 18:573-578, 2002).

Inflammation in the stomach and gastrointestinal tract is mediated by intercellular signal proteins known as cytokines which are produced by macrophages and dendritic cells in the epithelium in response to an antigenic stimulus such as that produced by *H. pylori* or other pathogens. Upon contact between the epithelium and the antigen such as *H. pylori* or endotoxins produced by it, such as LPS, antigen presenting cells (including dendritic cells) in the epithelium propagate the signal to naive macrophages which then respond in a so-called Th-1 type response where pro-inflammatory cytokines including TNF$\alpha$, IL-1, IL-6, IL-12 are produced by the macrophages. These cytokines in turn stimulate natural killer cells, T-cells and other cells to produce interferon $\gamma$ (IFN$\gamma$), which is the key mediator of inflammation. IFN$\gamma$ leads to an escalation of the inflammatory response and the reactions described above that lead to cytotoxicity. Naive macrophages can also respond to antigens with a Th-2 type response. This response is suppressed by IFN$\gamma$. These Th-2 type cells produce anti-inflammatory cytokines such as IL-4, IL-5, IL-9 and IL-10.

IL-10 is known to inhibit the production of IFN$\gamma$ and thus dampen the immune response. The balance between Th-1 and Th-2 type cells and their respective cytokine production defines the extent of the inflammation response to a given antigen. Th-2 type cells can also stimulate the production of immunoglobulins via the immune system. Anti-inflammatory activity in the gastrointestinal tract, where there is a reduced TNF$\alpha$ level, correlates with enhanced epithelial cells (gut wall lining integrity) and thus to a reduction in the negative effects caused by gastrointestinal pathogens and toxins.

The results of a number of research studies indicate that DNA can exert an anti-inflammatory action on intestinal epithelial cells, or can stimulate the immune system. (Madsen et al. and Rachmilewitz et al, respectively, presentations at Digestive Disease Week, May 19-22, 2002, The Moscone Center, San Francisco).

Mice spontaneously develop chronic colitis, which does not occur in germ-free animals. Mouse colitis is similar to human Crohn's disease, a chronic serious inflammatory disease of the gastrointestinal tract. Crohn's disease usually occurs in the intestines, but may occur anywhere in the gastrointestinal tract. These conditions require the presence of enteric bacteria and are both Th1-mediated-IL-12-dependent forms of colitis. Because of the similarities of the causes and symptoms, mouse models of colitis and other mouse models are used to study components of the inflammatory response directly, and are, as the same mechanisms apply in man, accepted to be used to develop treatments for human gastrointestinal disease.

*Lactobacillus reuteri* is one of the naturally occurring inhabitants of the gastrointestinal tract of animals and is routinely found in the intestines of healthy animals and despite the low pH, occasionally also in the human stomach. It is known to have antibacterial activity. See, for example U.S. Pat. Nos. 5,439,678, 5,458,875, 5,534,253, 5,837,238, and 5,849,289. When *L. reuteri* cells are grown under anaerobic conditions in the presence of glycerol, they produce the antimicrobial substance known as reuterin (β-hydroxy-propionaldehyde).

*L. coryniformis* is a less well-known species of *Lactobacillus* which is a rather common inhabitant of the human oral cavity. It can also be found in soil, manure and plant material. It has been found in silage and as a beer spoiler, and good lactic acid production has been reported as well as antifungal activity. The *L. coryniformis* MM7 isolate (ATCC PTA-4660) used herein was found in human mother's milk.

Immunomodulating activity has also been associated with various lactobacilli. While the possibility of effective antibacterial activity by several lactobacilli is known, it was not previously known that substantial differences existed between strains in their ability to reduce gastrointestinal inflammation, nor that such strains could be selected.

It is therefore an object of the invention to provide strains of *Lactobacillus* which have been selected for their capability of reducing gastrointestinal inflammation, such as that due to *Helicobacter pylori*. It is a further object of the invention to provide products containing said strains, including agents for treatment or prophylaxis of inflammation associated with *Helicobacter pylori* for administration to humans, including conditioned media in which said strains have grown and protein-containing extracts thereof.

Other objects and advantages will be more fully apparent from the following disclosure and appended claims.

SUMMARY OF THE INVENTION

The invention herein comprises certain *Lactobacillus* strains which have been selected for their capability of reducing gastrointestinal inflammation, such as that due to *Helicobacter pylori*, and products derived from said strains, including agents for treatment or prophylaxis of inflammation associated with *Helicobacter pylori* for administration to humans, and include conditioned media in which said strains have grown and protein-containing extracts of the conditioned media.

Other objects and features of the invention will be more fully apparent from the following disclosure and appended claims.

DETAILED DESCRIPTION OF THE INVENTION AND PREFERRED EMBODIMENTS THEREOF

Figure 1:
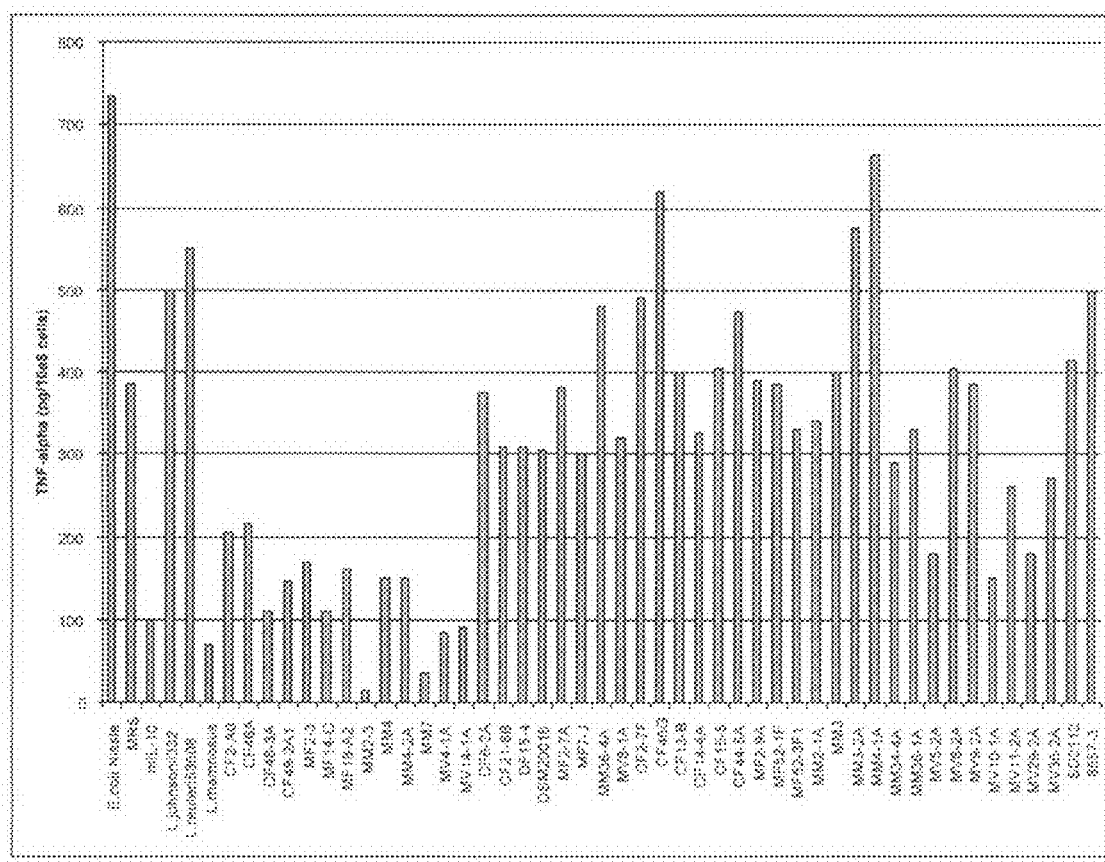
FIG. 1 is a bar graph showing the effect of *Lactobacillus*-conditioned media on TNFα production by LPS-activated macrophages. Forty-five *Lactobacillus* strains were tested.

The present invention herein comprises strains of *Lactobacillus* which have been selected for their capability of reducing gastrointestinal inflammation, such as that due to *Helicobacter pylori*. Such strains include *Lactobacillus coryniformis* MM7, ATCC PTA-4660 and *Lactobacillus reuteri* MM2-3, ATCC PTA-4659 deposited under the Budapest Treaty at the American Type Culture Collection, 10801 University Blvd., Manassas, Va. 20110-2209, on Sep. 11, 2002. Products such as foods, nutritional additives and formulations, pharmaceuticals or medical devices containing whole cells or components derived from these strains may be formulated as is known in the art, and generally include an ingestible support as known plus the *Lactobacillus*-strain, or its derived component. Previously known strains, now identified to have good TNFα reducing capacity, such as *L. rhamnosus* GG ATCC 53103, *L. reuteri* ATCC 55730 and others, can also be used in the above formulations. These products are agents for treatment or prophylaxis of inflammation associated with *Helicobacter pylori* for administration to mammals.

Model systems using the appropriate cytokines are used to determine factors that reduce or increase inflammation. In the examples provided herein, a mouse macrophage assay, using the RAW 264.7 macrophage cells (ATCC, Rockville, Md., ATCC # TIB-71), is used to screen strains of bacteria, primarily lactobacilli, for their effect on the inflammatory pathway. IL-10 is used in this assay as a positive control, with treatments with IL-10 showing inhibition of pro-inflammatory cytokines such as TNFα (tumor necrosis factor alpha). After individual growth of the *Lactobacillus* strains to be screened in laboratory media, the live bacterial cells are removed by filtration and the supernatant fluid (also called the "conditioned-medium" herein) is tested in the macrophage assay. The macrophages are first stimulated with the pro-inflammatory antigen for example, purified LPS (*E. coli* derived lipopolysaccharide), *S. aureus* derived lipoteichoic acid (LTA) or cell free *E. coli* or *Helicobacter* conditioned media, to produce the pro-inflammatory cytokines including TNFα. The conditioned medium from the *Lactobacillus* strain, containing the putative immunomodulating substances derived from the bacteria to be screened, is co-incubated with the antigen-activated macrophages. The capacity of the conditioned medium to modulate the immune response of the macrophages is monitored by the change in TNFα production by the cells. The TNFα profile from the assay enables a selection of the strains most effective in reducing the production of TNFα by the macrophages. Control experiments with pH adjustment in the assay system eliminates the possibility that a changed pH could cause the observed effect.

Surprisingly, apparently similar bacterial isolates and strains of *Lactobacillus*, even coming from very similar human sources show varying and widely different abilities to influence the production of TNFα by macrophages in response to a pro-inflammatory antigen. These strains cannot be identified even by genetic fingerprinting since they can be up to 98% similar genetically but still show very different effects on the immune cells. The strains thus screened and found to have a strong inhibitory effect against stimulated, pro-inflammatory cytokine production by macrophages are especially effective in the treatment of inflammation in the gastrointestinal tract of man, including *H. pylori* caused inflammation in the stomach.

The features of the present invention will be more clearly understood by reference to the following examples, which are not to be construed as limiting the invention.

EXAMPLE 1

Selection of Anti-Inflammatory Strains

*Lactobacillus* spp. (including for example *L. rhamnosus* GG ATCC 53103, *L. johnsonii* ATCC 33200, *L. reuteri* MM2-3 ATCC PTA-4659, *L. coryniformis*, MM7, ATCC PTA-4660) and *E. coli* Nissle were grown in de Man, Rogosa, Sharpe (MRS) and Luria-Bertani (LB) media (Difco, Sparks, Md.), respectively. Overnight cultures of lactobacilli were diluted to an $OD_{600}$ of 1.0 (representing approximately $10^9$ cells/ml) and further diluted 1:10 and grown for an additional 4, 8 and 24 h. *Helicobacter pylori*, (Sydney strain SS1) and *Helicobacter hepaticus* 3B1(ATCC 51449) were cultured for 48 h in Brucella broth (Difco) supplemented with 10% fetal bovine serum (FBS). Cultures were diluted 1:10 and grown for another 24 and 48 h. Bacterial cell-free conditioned medium was collected by centrifugation at 8500 rpm for 10 min at 4° C. Conditioned medium was separated from the cell pellet and then filtered through a 0.22 μm pore filter unit (Millipore, Bedford, Mass.).

Mouse monocyte/macrophage cell lines, RAW 264.7 (ATCC TIB-71) and RAW 264.7 gamma NO(−) (ATCC CRL-2278), were used as a reporter cells for studying the inflammatory response pathway. RAW 264.7 cells were grown in either Dulbecco's Modified Eagle Medium (wild-type) or RPMI Medium 1640 (gamma NO−) (Gibco-Invitrogen, Carlsbad, Calif.) supplemented with 10% FBS and 2% antibiotic (5000 units/ml Penicillin and 5 mg/ml Streptomycin, Sigma) at 5% $CO_2$ 37° C. until 80-90% confluent. Approximately $5 \times 10^4$ cells were seeded into 96-well cell culture clusters and allowed to adhere for 2 h prior to lipopolysaccharide (LPS) activation and addition of conditioned medium. Naive RAW 264.7 cells were exposed to purified LPS from *E. coli* serotype O127:B8 (Sigma). Activation medium was made by adding 2 ng LPS to 20 μl conditioned medium per well. Macrophages were either pre-incubated or co-incubated with cell-free *Lactobacillus* conditioned medium. Recombinant mIL-10 (R&D Systems, Minneapolis, Min.) was used as a positive control. Cell viability was assessed by Trypan-blue (Invitrogen) exclusion. The presence of TNF-α in cell culture supernatant was measured with a sandwich enzyme immunoassay, Quantikine M® Mouse TNF-α Immunoassay (R & D Systems).

Figure 2:
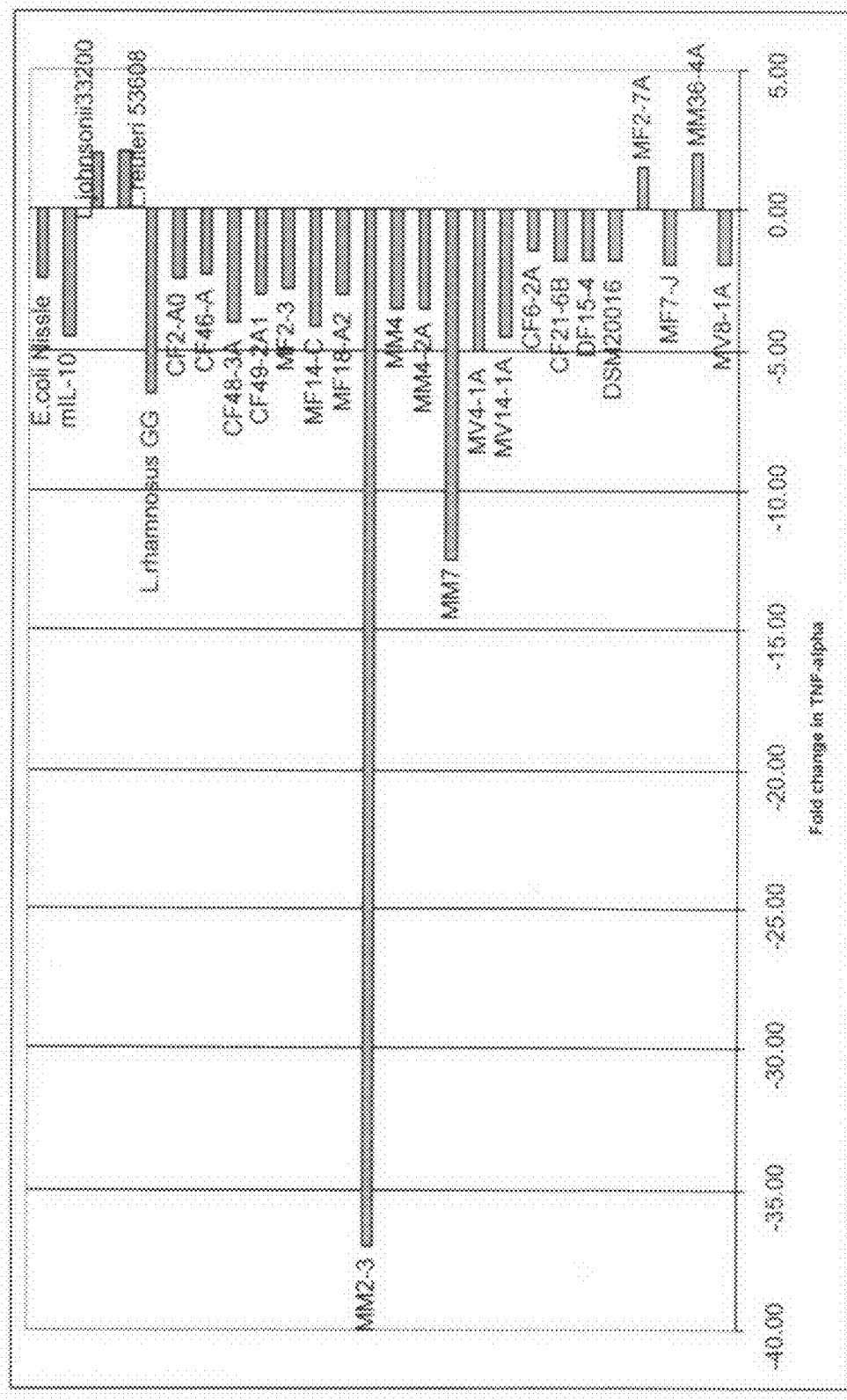
FIG. 2 is a bar graph showing the fold change in macrophage TNFα expression in the presence of conditioned media from various *Lactobacillus* strains and LPS compared to macrophages with LPS alone.

The effect of *Lactobacillus*-conditioned media on TNFα production by LPS-activated macrophages is shown in FIG. 1, which shows that of the 45 strains tested, several different strains are capable of decreasing TNFα production by the activated macrophages. FIG. 2 shows the fold change in TNFα expression with various *Lactobacillus* strains compared to LPS alone. The results of these studies are then used to select the most efficient strains. The strains mentioned in the figures but not specifically mentioned in the text are various strains of *Lactobacillus*, primarily *L. reuteri* that were tested.

In this example, *L. coryniformis* MM7, ATCC PTA-4660, was selected by using the method above, for addition to a standard yoghurt. The *L. coryniformis* strain was grown and lyophilized, using standard methods for growing *Lactobacillus* in the dairy industry. This culture was then added to previously fermented milk, using traditional yogurt cultures, at a level of 10E+7 CFU/gram of yogurt, and the yogurt was used by humans as a prevention of gastritis caused by *H. pylori*.

EXAMPLE 2

Use of the Conditioned Medium

Using the method above, the conditioned medium from one effectively TNFα decreasing strain was selected, in this experiment the medium from *L. reuteri* ATCC PTA-4659. This medium was produced in larger scale by growing the strain in de Man, Rogosa, Sharpe (MRS) (Difco, Sparks, Md.). Overnight cultures of lactobacilli were diluted to an $OD_{600}$ of 1.0 (representing approximately $10^9$ cells/ml) and further diluted 1:10 and grown for an additional 24 h. Bacterial cell-free conditioned medium was collected by centrifugation at 8500 rpm for 10 min at 4° C. Conditioned medium was separated from the cell pellet and then filtered through a 0.22 μm pore filter unit (Millipore, Bedford, Mass.). The conditioned medium was then lyophilized and formulated, using standard methods, to make a tablet. This tablet was used as a drug by humans to treat ulcer caused by *H. pylori*.

EXAMPLE 3

DNA-Fingerprinting of *Lactobacillus reuteri* Strains

The method of U.S. Pat. Nos. 5,523,217 and 5,691,136 of Lupski et al. was used to do genomic fingerprinting of *L. reuteri* strains. This method utilizes amplification of the bacterial DNA by adding a pair of outwardly-directed primers to the bacterial sample. After amplification, the extension products of the resulting hybridization are separated by size, and the strain of bacteria is characterized by measuring the pattern of sized extension products. Duplicate gel images were obtained for 82 strains of *L. reuteri* by Bacterial BarCodes, Inc. (Houston, Tex.) using the Uprime E primer (one primer) The duplicate sets of data were comparable. There were a total of 11 clusters, which were different from each other, and eight outliers, which appeared to be unique.

The strains found to be effective in reducing the TNF-α (see FIGS. 1 and 2) do not group together using this method, showing that it is not sufficient to use DNA-fingerprinting this way to find several strains with TNFα reducing capacity.

EXAMPLE 4

Characterization of Protein Produced by Effective *Lactobacillus* Strains

Different effective *Lactobacillus* conditioned media, including the *L. reuteri* strain MM2-3 conditioned medium, were treated with various denaturing compounds to determine the nature of the putative immunomodulins derived from the bacteria. Thus, conditioned media were subjected to repetitive freeze-thawing, heat treatment, digestion with DNA digesting enzymes, proteases and inactivated proteases. The putative immunomodulin was in this way determined to be one or more proteins or peptides in nature. To determine the size of the putative protein immunomodulin, the conditioned medium was fractionated by filtration and the filtrates tested for effectiveness. In this way, the active component of the conditioned media of effective *Lactobacillus* strains was found to be approx 5 kDa in size or less.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method for selecting a lactic acid bacterial strain for administration to a mammal for reducing gastrointestinal inflammation associated with *Helicobacter pylori* infection in the gastrointestinal tract of said mammal, comprising the steps of:
   a) selecting and culturing a *Lactobacillus* strain;
   b) obtaining a cell-free culture supernatant from said strain; and
   c) evaluating the level of TNFα in the supernatant using a model system.

* * * * *